(12) United States Patent
Tamori et al.

(10) Patent No.: US 8,846,877 B2
(45) Date of Patent: Sep. 30, 2014

(54) PACKING MATERIAL FOR AFFINITY CHROMATOGRAPHY

(75) Inventors: Kouji Tamori, Tsukuba (JP); Tetsuo Fukuta, Tsukuba (JP); Masaaki Miyaji, Tsukuba (JP); Yong Wang, Tsukuba (JP); Takayoshi Abe, Tsukuba (JP); Yuusuke Okano, Tsuchiura (JP); Masaki Momiyama, Tsukuba (JP); Takahiro Kawai, Tsuchiura (JP)

(73) Assignee: JSR Corporation, Tokyo (JP)

( * ) Notice: Subject to any disclaimer, the term of this patent is extended or adjusted under 35 U.S.C. 154(b) by 643 days.

(21) Appl. No.: 13/121,124

(22) PCT Filed: Sep. 24, 2009

(86) PCT No.: PCT/JP2009/066554
§ 371 (c)(1),
(2), (4) Date: Jul. 13, 2011

(87) PCT Pub. No.: WO2010/035757
PCT Pub. Date: Apr. 1, 2010

(65) Prior Publication Data
US 2011/0262748 A1    Oct. 27, 2011

(30) Foreign Application Priority Data

Sep. 25, 2008  (JP) ................. 2008-246154

(51) Int. Cl.
| | | |
|---|---|---|
| C07K 1/14 | (2006.01) | |
| G01N 33/544 | (2006.01) | |
| G01N 33/547 | (2006.01) | |
| B01J 20/32 | (2006.01) | |
| C07K 1/22 | (2006.01) | |
| B01J 20/286 | (2006.01) | |

(52) U.S. Cl.
CPC ............ *C07K 1/22* (2013.01); *B01J 20/3274* (2013.01); *B01J 20/321* (2013.01); *B01J 20/3219* (2013.01); *B01J 20/286* (2013.01)
USPC ........... 530/413; 436/528; 436/532; 530/412

(58) Field of Classification Search
CPC .. B01D 15/3809; B01D 15/3804; C07K 1/22; C07K 2317/00; A61K 39/385; A61K 39/44; A61K 2039/6093; C08L 51/00; C08L 63/10; B01J 20/3242; B01J 20/282; B01J 20/286
See application file for complete search history.

(56) References Cited

U.S. PATENT DOCUMENTS

| | | | |
|---|---|---|---|
| 4,336,173 A | | 6/1982 | Ugelstad |
| 4,459,378 A | | 7/1984 | Ugelstad |
| 5,059,654 A | * | 10/1991 | Hou et al. ................ 525/54.1 |
| 5,151,350 A | | 9/1992 | Colbert et al. |
| 2006/0030696 A1 | * | 2/2006 | Bonnerjea et al. ......... 530/387.1 |
| 2006/0194953 A1 | | 8/2006 | Bonnerjea et al. |
| 2008/0160167 A1 | | 7/2008 | Tamori et al. |
| 2010/0204424 A1 | | 8/2010 | Tamori et al. |
| 2011/0040075 A1 | | 2/2011 | Bonnerjea et al. |

FOREIGN PATENT DOCUMENTS

| | | |
|---|---|---|
| CN | 1771260 A | 5/2006 |
| EP | 1 837 656 A1 | 9/2007 |
| EP | 1992692 A1 * | 11/2008 |
| EP | 2 039 424 A1 | 3/2009 |
| GB | 2 184 732 A | 7/1987 |
| JP | 57 24369 | 5/1982 |
| JP | 63-159756 A | 7/1988 |
| JP | 06 281638 | 10/1994 |
| JP | 2006 304633 | 11/2006 |
| WO | 2007 142331 | 12/2007 |

OTHER PUBLICATIONS

Vaidya et al. Immobilization of candida rugosa lipase on poly(allyl glycidyl ether-co-ethylene glycol dimethacrylate) macroporous polymer particles, Bioresource Technology 2008, pp. 3623-3629.*
K. Terpe. Overview of tag protein fusions: from molecular and biochemical fundamentals to commercial systems. Appl Microbiol Biotechnol 2003, vol. 60, pp. 523-533.*
Poon et al. Reversible immunoprecipitation using histidine- or glutathio transferase- tagged *Staphylococcal* protein A, Analytical Biochemistry.1994, vol. 218, Abstract (pp. 1 and 2).*
Mateo et al. Immobilizaiton of enzymes on heterofunctional epoxy supports. Nature Protocols 2007, vol. 2, No. 2, pp. 1022-1033.*
Janknecht et al. Rapid and efficient purificaiton of native histidine-tagged protein expressed by recombinant vaccinia virus., PNAS 1991, vol. 88, pp. 8972-8976.*
U.S. Appl. No. 13/638,826, filed Oct. 1, 2012, Tamori, et al.
Hatakeyama, M., et al., "Polymer Particles as the Carrier for Affinity Purification," Japanese Journal of Polymer Science and Technology, vol. 64, No. 1, pp. 9-20, (Jan. 2007).
Moks, T., et al., "*Staphylococcal* protein a consists of five IgG-binding domains," European Journal of Biochemistry, vol. 156, No. 3, pp. 637-643, (May 1, 1986).
Bilici, Z., et al., "Activity behavior of a HPLC column including α-chymotrypsin immobilized monosized-porous particles," Analytica Chimica Acta, vol. 516, Issues 1-2, pp. 125-133, (May 25, 2004).
Inomata, Y., et al., "Purification of membrane receptors with peptide-carrying affinity latex particles," Colloids and Surfaces B: Biointerfaces, vol. 4, pp. 231-241, (1995).
International Search Report issued Dec. 15, 2009 in PCT/JP09/066554 filed Sep. 24, 2009.
U.S. Appl. No. 13/218,494, filed Aug. 26, 2011, Tamori, et al.

* cited by examiner

*Primary Examiner* — Shafiqul Haq
(74) *Attorney, Agent, or Firm* — Oblon, Spivak, McClelland, Maier & Neustadt, L.L.P.

(57) ABSTRACT

An affinity chromatography packing material includes porous mother particles that include a copolymer of a monomer mixture including a crosslinkable vinyl monomer and an epoxy group-containing vinyl monomer, a ligand being bound to the porous mother particles, and the porous mother particles including a ring-opening epoxy group produced by ring-opening of the epoxy group included in the porous mother particles.

15 Claims, 3 Drawing Sheets

FIG. 1

(SPAK)
NUMBER OF AMINO ACIDS: 159
MW: 18122.8748 Da

```
         R¹              r                              R²
                                              ——————— D-DOMAIN ———————
MKHHHHHHPMSDYDIPTTENLYFQGAMAKADAQQNNFNKDQQSAFYEILNMPNLNEAQRN

——————————— A-DOMAIN ———————————
GFIQSLKDDPSQSTNVLGEAKKLNESQAPKADNNFNKEQQNAFYEILNMPNLNEEQRNGF

IQSLKDDPSQSANLLSEAKKLNESQAPKADNKFNKEGSK*
```

(SPAC)
NUMBER OF AMINO ACIDS: 159
MW: 18079.8454 Da

```
         R¹              r                              R²
                                              ——————— D-DOMAIN ———————
MKHHHHHHPMSDYDIPTTENLYFQGAMAKADAQQNNFNKDQQSAFYEILNMPNLNEAQRN

——————————— A-DOMAIN ———————————
GFIQSLKDDPSQSTNVLGEAKKLNESQAPKADNNFNKEQQNAFYEILNMPNLNEEQRNGF

IQSLKDDPSQSANLLSEAKKLNESQAPKADNKFNKEGSC*
```

(SPAKK)
NUMBER OF AMINO ACIDS: 163
MW: 18635.5716 Da

```
         R¹              r                              R²
                                              ——————— D-DOMAIN ———————
MKHHHHHHPMSDYDIPTTENLYFQGAMAKADAQQNNFNKDQQSAFYEILNMPNLNEAQRN

——————————— A-DOMAIN ———————————
GFIQSLKDDPSQSTNVLGEAKKLNESQAPKADNNFNKEQQNAFYEILNMPNLNEEQRNGF

IQSLKDDPSQSANLLSEAKKLNESQAPKADNKFNKEGSKKKKK*
```

(SPATK)
NUMBER OF AMINO ACIDS: 291
MW: 32914.9668 Da

```
         R¹              r                              R²
                                              ——————— D-DOMAIN ———————
MKHHHHHHPMSDYDIPTTENLYFQGAMAKADAQQNNFNKDQQSAFYEILNMPNLNEAQRN

——————————— A-DOMAIN ———————————
GFIQSLKDDPSQSTNVLGEAKKLNESQAPKADNNFNKEQQNAFYEILNMPNLNEEQRNGF

——————— D-DOMAIN ———————
IQSLKDDPSQSANLLSEAKKLNESQAPKADNKFNKEGSSGKADAQQNNFNKDQQSAFYEI

——————————— A-DOMAIN ———————————
LNMPNLNEAQRNGFIQSLKDDPSQSTNVLGEAKKLNESQAPKADNNFNKEQQNAFYEILN

MPNLNEEQRNGFIQSLKDDPSQSANLLSEAKKLNESQAPKADNKFNKEGSK*
```

FIG. 2

(SPA2K)
NUMBER OF AMINO ACIDS: 160
MW: 18251.049 Da

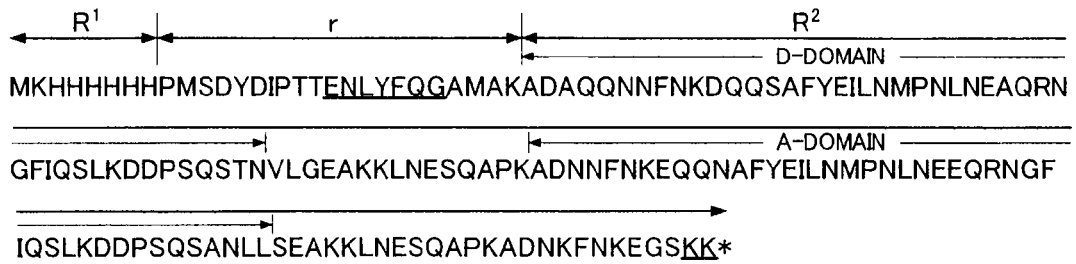

MKHHHHHHPMSDYDIPTTENLYFQGAMAKADAQQNNFNKDQQSAFYEILNMPNLNEAQRN
GFIQSLKDDPSQSTNVLGEAKKLNESQAPKADNNFNKEQQNAFYEILNMPNLNEEQRNGF
IQSLKDDPSQSANLLSEAKKLNESQAPKADNKFNKEGSKK*

(SPA3K)
NUMBER OF AMINO ACIDS: 161
MW: 18379.2232 Da

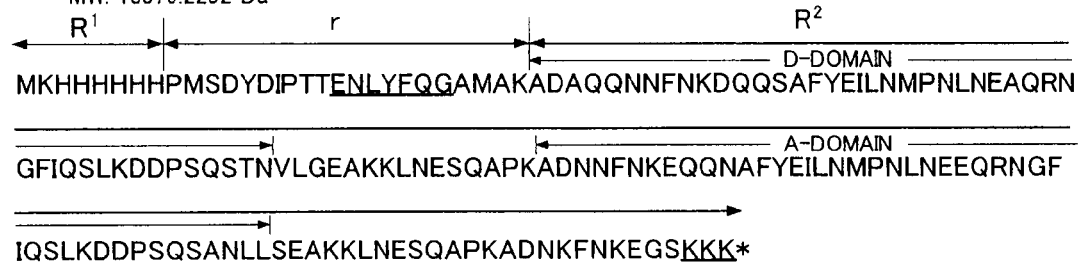

MKHHHHHHPMSDYDIPTTENLYFQGAMAKADAQQNNFNKDQQSAFYEILNMPNLNEAQRN
GFIQSLKDDPSQSTNVLGEAKKLNESQAPKADNNFNKEQQNAFYEILNMPNLNEEQRNGF
IQSLKDDPSQSANLLSEAKKLNESQAPKADNKFNKEGSKKK*

(SPA-His-C)
NUMBER OF AMINO ACIDS: 141
MW: 16051.769Da

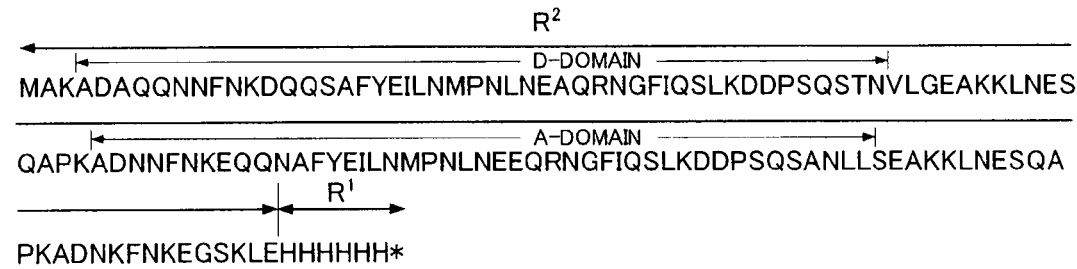

MAKADAQQNNFNKDQQSAFYEILNMPNLNEAQRNGFIQSLKDDPSQSTNVLGEAKKLNES
QAPKADNNFNKEQQNAFYEILNMPNLNEEQRNGFIQSLKDDPSQSANLLSEAKKLNESQA
PKADNKFNKEGSKLEHHHHHH*

(SPA-His-N)
NUMBER OF AMINO ACIDS: 142
MW: 16175.7653 Da

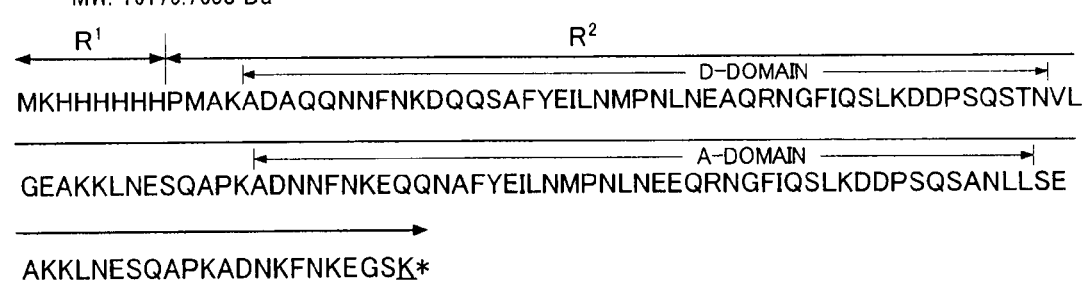

MKHHHHHHPMAKADAQQNNFNKDQQSAFYEILNMPNLNEAQRNGFIQSLKDDPSQSTNVL
GEAKKLNESQAPKADNNFNKEQQNAFYEILNMPNLNEEQRNGFIQSLKDDPSQSANLLSE
AKKLNESQAPKADNKFNKEGSK*

```
                        SEQUENCE LISTING

<160> NUMBER OF SEQ ID NOS: 26

<210> SEQ ID NO 1
<211> LENGTH: 159
<212> TYPE: PRT
<213> ORGANISM: Artificial Sequence
<220> FEATURE:
<223> OTHER INFORMATION: Description of Artificial Sequence: Synthetic
      immunoglobulin-binding protein sequence

<400> SEQUENCE: 1

Met Lys His His His His His His Pro Met Ser Asp Tyr Asp Ile Pro
1               5                   10                  15

Thr Thr Glu Asn Leu Tyr Phe Gln Gly Ala Met Ala Lys Ala Asp Ala
            20                  25                  30

Gln Gln Asn Asn Phe Asn Lys Asp Gln Gln Ser Ala Phe Tyr Glu Ile
        35                  40                  45

Leu Asn Met Pro Asn Leu Asn Glu Ala Gln Arg Asn Gly Phe Ile Gln
    50                  55                  60

Ser Leu Lys Asp Asp Pro Ser Gln Ser Thr Asn Val Leu Gly Glu Ala
65                  70                  75                  80

Lys Lys Leu Asn Glu Ser Gln Ala Pro Lys Ala Asp Asn Asn Phe Asn
                85                  90                  95

Lys Glu Gln Gln Asn Ala Phe Tyr Glu Ile Leu Asn Met Pro Asn Leu
            100                 105                 110

Asn Glu Glu Gln Arg Asn Gly Phe Ile Gln Ser Leu Lys Asp Asp Pro
        115                 120                 125

Ser Gln Ser Ala Asn Leu Leu Ser Glu Ala Lys Lys Leu Asn Glu Ser
    130                 135                 140

Gln Ala Pro Lys Ala Asp Asn Lys Phe Asn Lys Glu Gly Ser Lys
145                 150                 155

<210> SEQ ID NO 2
<211> LENGTH: 159
<212> TYPE: PRT
<213> ORGANISM: Artificial Sequence
<220> FEATURE:
<223> OTHER INFORMATION: Description of Artificial Sequence: Synthetic
      immunoglobulin-binding protein sequence

<400> SEQUENCE: 2

Met Lys His His His His His His Pro Met Ser Asp Tyr Asp Ile Pro
1               5                   10                  15
```

Thr Thr Glu Asn Leu Tyr Phe Gln Gly Ala Met Ala Lys Ala Asp Ala
            20                  25                  30

Gln Gln Asn Asn Phe Asn Lys Asp Gln Gln Ser Ala Phe Tyr Glu Ile
        35                  40                  45

Leu Asn Met Pro Asn Leu Asn Glu Ala Gln Arg Asn Gly Phe Ile Gln
50                  55                  60

Ser Leu Lys Asp Asp Pro Ser Gln Ser Thr Asn Val Leu Gly Glu Ala
65                  70                  75                  80

Lys Lys Leu Asn Glu Ser Gln Ala Pro Lys Ala Asp Asn Asn Phe Asn
            85                  90                  95

Lys Glu Gln Gln Asn Ala Phe Tyr Glu Ile Leu Asn Met Pro Asn Leu
            100                 105                 110

Asn Glu Glu Gln Arg Asn Gly Phe Ile Gln Ser Leu Lys Asp Asp Pro
            115                 120                 125

Ser Gln Ser Ala Asn Leu Leu Ser Glu Ala Lys Lys Leu Asn Glu Ser
        130                 135                 140

Gln Ala Pro Lys Ala Asp Asn Lys Phe Asn Lys Glu Gly Ser Cys
145                 150                 155

<210> SEQ ID NO 3
<211> LENGTH: 163
<212> TYPE: PRT
<213> ORGANISM: Artificial Sequence
<220> FEATURE:
<223> OTHER INFORMATION: Description of Artificial Sequence: Synthetic
      immunoglobulin-binding protein sequence

<400> SEQUENCE: 3

Met Lys His His His His His His Pro Met Ser Asp Tyr Asp Ile Pro
1               5                   10                  15

Thr Thr Glu Asn Leu Tyr Phe Gln Gly Ala Met Ala Lys Ala Asp Ala
            20                  25                  30

Gln Gln Asn Asn Phe Asn Lys Asp Gln Gln Ser Ala Phe Tyr Glu Ile
        35                  40                  45

Leu Asn Met Pro Asn Leu Asn Glu Ala Gln Arg Asn Gly Phe Ile Gln
50                  55                  60

Ser Leu Lys Asp Asp Pro Ser Gln Ser Thr Asn Val Leu Gly Glu Ala
65                  70                  75                  80

Lys Lys Leu Asn Glu Ser Gln Ala Pro Lys Ala Asp Asn Asn Phe Asn
            85                  90                  95

Lys Glu Gln Gln Asn Ala Phe Tyr Glu Ile Leu Asn Met Pro Asn Leu
            100                 105                 110

Asn Glu Glu Gln Arg Asn Gly Phe Ile Gln Ser Leu Lys Asp Asp Pro
            115                 120                 125

Ser Gln Ser Ala Asn Leu Leu Ser Glu Ala Lys Lys Leu Asn Glu Ser
        130                 135                 140

Gln Ala Pro Lys Ala Asp Asn Lys Phe Asn Lys Glu Gly Ser Lys Lys
145                 150                 155                 160

Lys Lys Lys

<210> SEQ ID NO 4
<211> LENGTH: 291
<212> TYPE: PRT
<213> ORGANISM: Artificial Sequence
<220> FEATURE:
<223> OTHER INFORMATION: Description of Artificial Sequence: Synthetic
      immunoglobulin-binding protein sequence

<400> SEQUENCE: 4

```
Met Lys His His His His His Pro Met Ser Asp Tyr Asp Ile Pro
1               5                   10                  15

Thr Thr Glu Asn Leu Tyr Phe Gln Gly Ala Met Ala Lys Ala Asp Ala
            20                  25                  30

Gln Gln Asn Asn Phe Asn Lys Asp Gln Gln Ser Ala Phe Tyr Glu Ile
            35                  40                  45

Leu Asn Met Pro Asn Leu Asn Glu Ala Gln Arg Asn Gly Phe Ile Gln
50                  55                  60

Ser Leu Lys Asp Asp Pro Ser Gln Ser Thr Asn Val Leu Gly Glu Ala
65                  70                  75                  80

Lys Lys Leu Asn Glu Ser Gln Ala Pro Lys Ala Asp Asn Asn Phe Asn
                85                  90                  95

Lys Glu Gln Gln Asn Ala Phe Tyr Glu Ile Leu Asn Met Pro Asn Leu
            100                 105                 110

Asn Glu Glu Gln Arg Asn Gly Phe Ile Gln Ser Leu Lys Asp Asp Pro
            115                 120                 125

Ser Gln Ser Ala Asn Leu Leu Ser Glu Ala Lys Lys Leu Asn Glu Ser
130                 135                 140

Gln Ala Pro Lys Ala Asp Asn Lys Phe Asn Lys Glu Gly Ser Ser Gly
145                 150                 155                 160

Lys Ala Asp Ala Gln Gln Asn Asn Phe Asn Lys Asp Gln Gln Ser Ala
                165                 170                 175

Phe Tyr Glu Ile Leu Asn Met Pro Asn Leu Asn Glu Ala Gln Arg Asn
            180                 185                 190

Gly Phe Ile Gln Ser Leu Lys Asp Asp Pro Ser Gln Ser Thr Asn Val
            195                 200                 205

Leu Gly Glu Ala Lys Lys Leu Asn Glu Ser Gln Ala Pro Lys Ala Asp
210                 215                 220

Asn Asn Phe Asn Lys Glu Gln Gln Asn Ala Phe Tyr Glu Ile Leu Asn
225                 230                 235                 240

Met Pro Asn Leu Asn Glu Glu Gln Arg Asn Gly Phe Ile Gln Ser Leu
                245                 250                 255

Lys Asp Asp Pro Ser Gln Ser Ala Asn Leu Leu Ser Glu Ala Lys Lys
            260                 265                 270

Leu Asn Glu Ser Gln Ala Pro Lys Ala Asp Asn Lys Phe Asn Lys Glu
            275                 280                 285

Gly Ser Lys
    290
```

<210> SEQ ID NO 5
<211> LENGTH: 160
<212> TYPE: PRT
<213> ORGANISM: Artificial Sequence
<220> FEATURE:
<223> OTHER INFORMATION: Description of Artificial Sequence: Synthetic immunoglobulin-binding protein sequence

<400> SEQUENCE: 5

```
Met Lys His His His His His Pro Met Ser Asp Tyr Asp Ile Pro
1               5                   10                  15

Thr Thr Glu Asn Leu Tyr Phe Gln Gly Ala Met Ala Lys Ala Asp Ala
            20                  25                  30

Gln Gln Asn Asn Phe Asn Lys Asp Gln Gln Ser Ala Phe Tyr Glu Ile
            35                  40                  45
```

```
Leu Asn Met Pro Asn Leu Asn Glu Ala Gln Arg Asn Gly Phe Ile Gln
 50                  55                  60

Ser Leu Lys Asp Asp Pro Ser Gln Ser Thr Asn Val Leu Gly Glu Ala
 65                  70                  75                  80

Lys Lys Leu Asn Glu Ser Gln Ala Pro Lys Ala Asp Asn Asn Phe Asn
                 85                  90                  95

Lys Glu Gln Gln Asn Ala Phe Tyr Glu Ile Leu Asn Met Pro Asn Leu
                100                 105                 110

Asn Glu Glu Gln Arg Asn Gly Phe Ile Gln Ser Leu Lys Asp Asp Pro
            115                 120                 125

Ser Gln Ser Ala Asn Leu Leu Ser Glu Ala Lys Lys Leu Asn Glu Ser
        130                 135                 140

Gln Ala Pro Lys Ala Asp Asn Lys Phe Asn Lys Glu Gly Ser Lys Lys
145                 150                 155                 160
```

<210> SEQ ID NO 6
<211> LENGTH: 161
<212> TYPE: PRT
<213> ORGANISM: Artificial Sequence
<220> FEATURE:
<223> OTHER INFORMATION: Description of Artificial Sequence: Synthetic
      immunoglobulin-binding protein sequence

<400> SEQUENCE: 6

```
Met Lys His His His His His His Pro Met Ser Asp Tyr Asp Ile Pro
 1               5                  10                  15

Thr Thr Glu Asn Leu Tyr Phe Gln Gly Ala Met Ala Lys Ala Asp Ala
                 20                  25                  30

Gln Gln Asn Asn Phe Asn Lys Asp Gln Gln Ser Ala Phe Tyr Glu Ile
             35                  40                  45

Leu Asn Met Pro Asn Leu Asn Glu Ala Gln Arg Asn Gly Phe Ile Gln
 50                  55                  60

Ser Leu Lys Asp Asp Pro Ser Gln Ser Thr Asn Val Leu Gly Glu Ala
 65                  70                  75                  80

Lys Lys Leu Asn Glu Ser Gln Ala Pro Lys Ala Asp Asn Asn Phe Asn
                 85                  90                  95

Lys Glu Gln Gln Asn Ala Phe Tyr Glu Ile Leu Asn Met Pro Asn Leu
                100                 105                 110

Asn Glu Glu Gln Arg Asn Gly Phe Ile Gln Ser Leu Lys Asp Asp Pro
            115                 120                 125

Ser Gln Ser Ala Asn Leu Leu Ser Glu Ala Lys Lys Leu Asn Glu Ser
        130                 135                 140

Gln Ala Pro Lys Ala Asp Asn Lys Phe Asn Lys Glu Gly Ser Lys Lys
145                 150                 155                 160

Lys
```

<210> SEQ ID NO 7
<211> LENGTH: 141
<212> TYPE: PRT
<213> ORGANISM: Artificial Sequence
<220> FEATURE:
<223> OTHER INFORMATION: Description of Artificial Sequence: Synthetic
      immunoglobulin-binding protein sequence

<400> SEQUENCE: 7

```
Met Ala Lys Ala Asp Ala Gln Gln Asn Asn Phe Asn Lys Asp Gln Gln
 1               5                  10                  15

Ser Ala Phe Tyr Glu Ile Leu Asn Met Pro Asn Leu Asn Glu Ala Gln
```

```
                    20                  25                  30
Arg Asn Gly Phe Ile Gln Ser Leu Lys Asp Asp Pro Ser Gln Ser Thr
            35                  40                  45

Asn Val Leu Gly Glu Ala Lys Lys Leu Asn Glu Ser Gln Ala Pro Lys
        50                  55                  60

Ala Asp Asn Asn Phe Asn Lys Glu Gln Gln Asn Ala Phe Tyr Glu Ile
65                  70                  75                  80

Leu Asn Met Pro Asn Leu Asn Glu Glu Gln Arg Asn Gly Phe Ile Gln
                85                  90                  95

Ser Leu Lys Asp Asp Pro Ser Gln Ser Ala Asn Leu Leu Ser Glu Ala
            100                 105                 110

Lys Lys Leu Asn Glu Ser Gln Ala Pro Lys Ala Asp Asn Lys Phe Asn
        115                 120                 125

Lys Glu Gly Ser Lys Leu Glu His His His His His
    130                 135                 140
```

<210> SEQ ID NO 8
<211> LENGTH: 142
<212> TYPE: PRT
<213> ORGANISM: Artificial Sequence
<220> FEATURE:
<223> OTHER INFORMATION: Description of Artificial Sequence: Synthetic
      immunoglobulin-binding protein sequence

<400> SEQUENCE: 8

```
Met Lys His His His His His His Pro Met Ala Lys Ala Asp Ala Gln
1               5                   10                  15

Gln Asn Asn Phe Asn Lys Asp Gln Gln Ser Ala Phe Tyr Glu Ile Leu
                20                  25                  30

Asn Met Pro Asn Leu Asn Glu Ala Gln Arg Asn Gly Phe Ile Gln Ser
            35                  40                  45

Leu Lys Asp Asp Pro Ser Gln Ser Thr Asn Val Leu Gly Glu Ala Lys
        50                  55                  60

Lys Leu Asn Glu Ser Gln Ala Pro Lys Ala Asp Asn Phe Asn Lys
65                  70                  75                  80

Glu Gln Gln Asn Ala Phe Tyr Glu Ile Leu Asn Met Pro Asn Leu Asn
                85                  90                  95

Glu Glu Gln Arg Asn Gly Phe Ile Gln Ser Leu Lys Asp Asp Pro Ser
            100                 105                 110

Gln Ser Ala Asn Leu Leu Ser Glu Ala Lys Lys Leu Asn Glu Ser Gln
        115                 120                 125

Ala Pro Lys Ala Asp Asn Lys Phe Asn Lys Glu Gly Ser Lys
    130                 135                 140
```

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
catgccatgg cgaaagctga tgcgcaacaa aat         33

<210> SEQ ID NO 10
<211> LENGTH: 44
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 10
cccaagcttt tacttggatc cttctttgtt gaatttgtta tccg                    44

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cccaagcttt tagcaggatc cttctttgtt gaatttgtta tccg                    44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cccaagcttt tacttcttgg atccttcttt gttgaatttg ttat                    44

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cccaagcttt tacttcttct tggatccttc tttgttgaat tgttat                  47

<210> SEQ ID NO 14
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccaagcttt tatttctttt tcttcttgga tccttctttg ttgaatttgt tat          53

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cggggatcct caggcaaagc tgatgcgcaa caaaat                             36

<210> SEQ ID NO 16
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 16
ccccatatgg cgaaagctga tgcgcaaa                                              28

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gggctcgagc ttggatcctt ctttgtt                                               27

<210> SEQ ID NO 18
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Ala Met Ala Lys Ala Asp Ala Gln Gln Asn Asn Phe Asn Lys Asp
1               5                   10                  15

Gln Gln Ser Ala Phe Tyr Glu Ile Leu Asn Met Pro Asn Leu Asn Glu
            20                  25                  30

Ala Gln Arg Asn Gly Phe Ile Gln Ser Leu Lys Asp Asp Pro Ser Gln
        35                  40                  45

Ser Thr Asn Val Leu Gly Glu Ala Lys Lys Leu Asn Glu Ser Gln Ala
    50                  55                  60

Pro Lys Ala Asp Asn Asn Phe Asn Lys Glu Gln Gln Asn Ala Phe Tyr
65                  70                  75                  80

Glu Ile Leu Asn Met Pro Asn Leu Asn Glu Glu Gln Arg Asn Gly Phe
                85                  90                  95

Ile Gln Ser Leu Lys Asp Asp Pro Ser Gln Ser Ala Asn Leu Leu Ser
            100                 105                 110

Glu Ala Lys Lys Leu Asn Glu Ser Gln Ala Pro Lys Ala Asp Asn Lys
        115                 120                 125

Phe Asn Lys Glu Gly Ser Lys
    130                 135

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This sequence may encompass 4-20 residues

<400> SEQUENCE: 19

His His His His His His His His His His His His His His His His
1               5                   10                  15

His His His His
            20
```

```
<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

His His His His
1

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(8)
<223> OTHER INFORMATION: This sequence may encompass 4-8 residues

<400> SEQUENCE: 21

His His His His His His His His
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 22

His His His His His His
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Asn Leu Tyr Phe Gln Gly
1               5

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ser Ser Gly
1

<210> SEQ ID NO 25
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 25

Lys Lys Lys Lys Lys
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys His His His His His His
1               5
```

PACKING MATERIAL FOR AFFINITY CHROMATOGRAPHY

CROSS-REFERENCE TO RELATED APPLICATIONS

The present application is a 35 U.S.C. §371 National Stage patent application of International patent application PCT/JP2009/066554, filed on Sep. 24, 2009, which claims priority to Japanese patent application JP 2008-246154, filed on Sep. 25, 2008.

TECHNICAL FIELD

The present invention relates to an affinity chromatography packing material. More specifically, the invention relates to an affinity chromatography packing material to which a specific ligand useful for antibody purification is bound.

BACKGROUND ART

Affinity chromatography utilizes a column charged with a ligand-bound carrier (i.e., an insoluble carrier on which a substance (ligand) that specifically binds to the separation/purification target substance is immobilized). For example, affinity chromatography has been used to separate and purify biological substances such as proteins and nucleic acids (see JP-A-6-281638).

Crosslinked particles of sugar chains such as agarose gel have been widely used as the affinity chromatography packing material. However, such particles may be deformed and increase the column pressure when a solution containing the separation/purification target molecules is passed through the column at a high flow rate, so that the separation/purification efficiency may deteriorate.

An affinity chromatography packing material "POROS" (manufactured by Applied Biosystems) can be used at a relatively high flow rate. This packing material includes mother particles that contain a hydrophobic styrene-divinylbenzene copolymer as the main component. When using this packing material, non-specific adsorption that is considered to be mainly caused by the mother particles may occur. Moreover, the binding capacity may decrease when the packing material is used at a high flow rate.

SUMMARY OF INVENTION

Technical Problem

An object of the invention is to provide an affinity chromatography packing material that can maintain a high ligand binding capacity even when used for separation and purification at a high flow rate.

Solution to Problem

According to one aspect of the invention, there is provided an affinity chromatography packing material including porous mother particles that include a copolymer of a monomer mixture including a crosslinkable vinyl monomer and an epoxy group-containing vinyl monomer, a ligand being bound to the porous mother particles, and the porous mother particles including a ring-opening epoxy group produced by ring-opening of the epoxy group included in the porous mother particles.

In the above affinity chromatography packing material, the ring-opening epoxy group may be a substituted or unsubstituted 2,3-dihydroxypropyl group.

In the above affinity chromatography packing material, the ligand may be a protein that includes an immunoglobulin-binding domain of protein A.

In this case, the immunoglobulin-binding domain of protein A may be at least one immunoglobulin-binding domain selected from an A-domain, a B-domain, a C-domain, a D-domain, an E-domain, and a Z-domain.

In the above affinity chromatography packing material, the ligand may be an immunoglobulin-binding protein shown by the following general formula (1), $$R\text{-}R^2 \qquad (1)$$

wherein R represents an amino acid sequence that includes 4 to 300 amino acids and includes a site including 4 to 20 consecutive histidine residues (SEQ ID NO: 19), and $R^2$ represents an amino acid sequence that includes 50 to 500 amino acids and includes at least one immunoglobulin-binding domain of protein A, provided that a terminal of the immunoglobulin-binding domain binds to R.

In this case, R- in the general formula (1) may be a group shown by the following general formula (2), $$R^1\text{-}r\text{-} \qquad (2)$$

wherein $R^1$ represents an amino acid sequence that includes 4 to 100 amino acids and includes a site including 4 to 20 consecutive histidine residues(SEQ ID NO: 19), provided that a terminal of the site including 4 to 20 consecutive histidine residues (SEQ ID NO: 19) binds to r, and r represents an arbitrary amino acid sequence that includes 7 to 200 amino acids and includes a TEV domain.

At least one of the amino acid sequence represented by R and the amino acid sequence represented by $R^2$ in the general formula (1) may include a domain t that includes 1 to 50 amino acids and includes one amino acid selected from lysine, arginine, and cysteine.

In the above affinity chromatography packing material, the ligand may be an immunoglobulin-binding protein shown by the following general formula (3), $$R^2\text{-}R \qquad (3)$$

wherein R represents an amino acid sequence that includes 4 to 300 amino acids and includes a site including 4 to 20 consecutive histidine residues (SEQ ID NO: 19), and $R^2$ represents an amino acid sequence that includes 50 to 500 amino acids and includes at least one immunoglobulin-binding domain of protein A, provided that a terminal of the immunoglobulin-binding domain binds to R.

In this case, -R in the general formula (3) may be a group shown by the following general formula (4), $$\text{-}r\text{-}R^1 \qquad (4)$$

wherein $R^1$ represents an amino acid sequence that includes 4 to 100 amino acids and includes a site including 4 to 20 consecutive histidine residues (SEQ ID NO: 19), provided that a terminal of the site including 4 to 20 consecutive histidine residues (SEQ ID NO: 19) binds to r, and r represents an arbitrary amino acid sequence that includes 7 to 200 amino acids and includes a TEV domain.

At least one of the amino acid sequence represented by R and the amino acid sequence represented by $R^2$ in the general formula (3) may include a domain t that includes 1 to 50 amino acids and includes one amino acid selected from lysine, arginine, and cysteine.

The term "protein" used herein refers to a molecule that includes a peptide structural unit, and includes a fragment of a natural protein, and a variant obtained by artificially altering the amino acid sequence of a natural protein. The term "immunoglobulin-binding domain" used herein refers to a functional unit of a polypeptide that has an immunoglobulin avidity. The term "immunoglobulin-binding protein" used herein refers to a protein that exhibits a specific affinity to immunoglobulin, and includes an immunoglobulin-binding domain.

The term "TEV domain" used herein refers to a cleavage site due to a tobacco etch virus (TEV) protease.

Advantageous Effects of Invention

Since the above affinity chromatography packing material includes porous mother particles that include a copolymer of a monomer mixture including a crosslinkable vinyl monomer and an epoxy group-containing vinyl monomer, a ligand being bound to the porous mother particles, and the porous mother particles including a ring-opening epoxy group produced by ring-opening of the epoxy group included in the porous mother particles, the affinity chromatography packing material can maintain a high ligand binding capacity even when used for separation and purification at a high flow rate.

BRIEF DESCRIPTION OF DRAWINGS

FIG. 1 illustrates the amino acid sequences of immunoglobulin-binding proteins (SPAK (SEQ ID NO: 1), SPAC (SEQ ID NO: 2), SPAKK (SEQ ID NO: 3), and SPATK (SEQ ID NO: 4)) produced in Synthesis Example 1.

FIG. 2 illustrates the amino acid sequences of immunoglobulin-binding proteins (SPA2K (SEQ ID NO: 5), SPA3K (SEQ ID NO: 6), SPA-His-C (SEQ ID NO: 7), and SPA-His-N (SEQ ID NO: 8)) produced in Synthesis Example 1.

FIG. 3 discloses "6×His," "GSSG," "Lys-Lys-Lys-Lys-Lys" and "Lys- 6×His" as SEQ ID NOS: 22 and 24-26, respectively.

DESCRIPTION OF EMBODIMENTS

Figure 3:
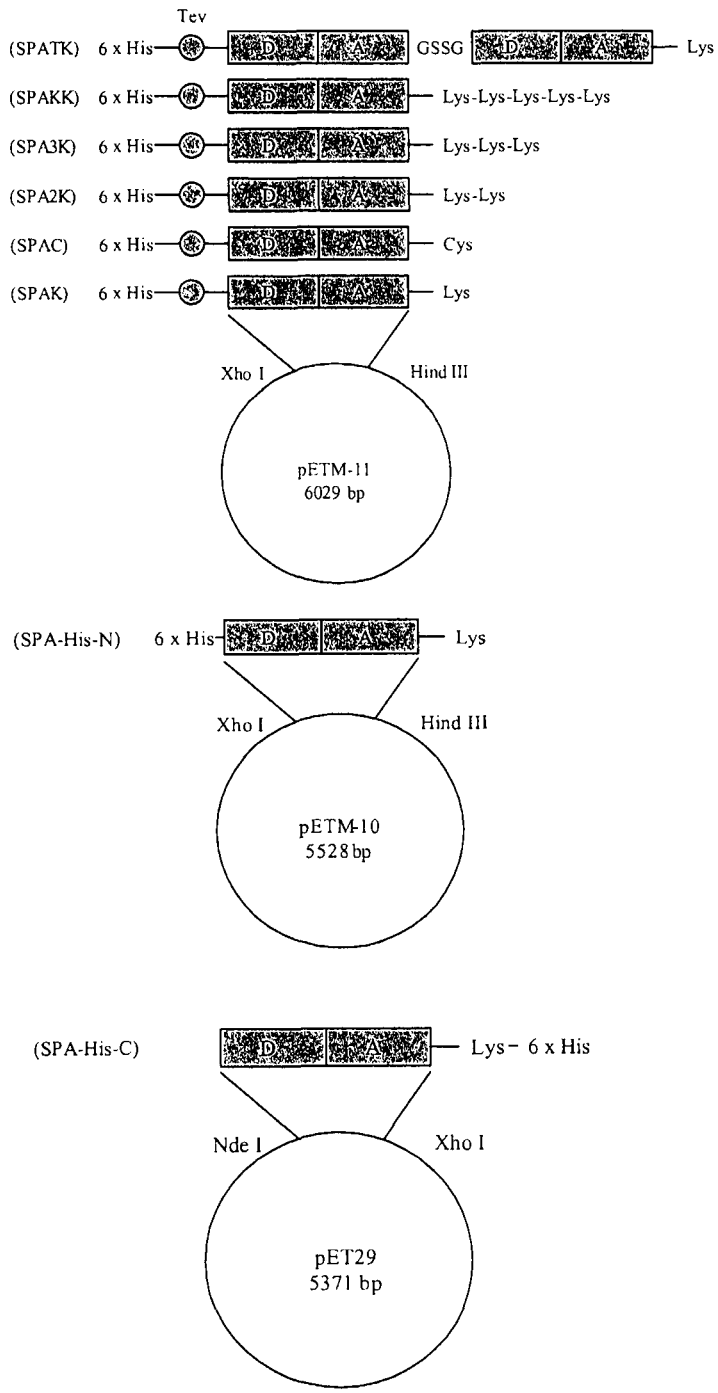
FIG. 3 illustrates the configuration of a DNA fragment that encodes an immunoglobulin-binding protein produced in Synthesis Example 1 and is inserted into an expression vector (pETM-11, pETM-10, and pET29).

An affinity chromatography packing material according to one embodiment of the invention includes porous mother particles that include a copolymer of a monomer mixture including a crosslinkable vinyl monomer and an epoxy group-containing vinyl monomer, a ligand being bound to the porous mother particles, and the porous mother particles including a ring-opening epoxy group produced by ring-opening of the epoxy group included in the porous mother particles.

1. Affinity Chromatography Packing Material 1.1. Porous Mother Particles 1.1.1. Configuration It is preferable that the affinity chromatography packing material (porous mother particles) according to one embodiment of the invention mainly include a copolymer of a monomer mixture including a crosslinkable vinyl monomer and an epoxy group-containing vinyl monomer.

An aromatic polyvinyl monomer and an aliphatic polyvinyl monomer are preferable as the crosslinkable vinyl monomer. Divinylbenzene is preferable as the aromatic polyvinyl monomer, and a poly(meth)acrylate compound is preferable as the aliphatic polyvinyl monomer. Examples of the poly(meth)acrylate compound include ethylene glycol di(meth)acrylate, diethylene glycol di(meth)acrylate, triethylene glycol di(meth)acrylate, tetraethylene glycol di(meth)acrylate, propylene glycol di(meth)acrylate, dipropylene glycol di(meth)acrylate, tripropylene glycol di(meth)acrylate, tetrapropylene glycol di(meth)acrylate, 1,4-butanediol di(meth)acrylate, 1,6-hexanediol di(meth)acrylate, trimethylolpropane tri(meth)acrylate, pentaerythritol tetra(meth)acrylate, and the like. Among these, trimethylolpropane trimethacrylate, trimethylolpropane triacrylate, ethylene glycol dimethacrylate, and ethylene glycol diacrylate are preferable.

The epoxy group-containing vinyl monomer is a vinyl monomer that includes an epoxy group in the molecule. Examples of the epoxy group-containing vinyl monomer include (meth)acrylates such as glycidyl (meth)acrylate and alpha-(meth)acryl-omega-glycidyl polyethylene glycol; aromatic vinyl compounds such as vinylbenzyl glycidyl ether; and the like. Among these, glycidyl methacrylate and vinylbenzyl glycidyl ether are preferable.

It is preferable to use porous organic polymer particles that include a copolymer of 20 to 50 wt % of the crosslinkable vinyl monomer and 50 to 80 wt % of the epoxy group-containing vinyl monomer as the affinity chromatography packing material according to one embodiment of the invention. If the amount of the crosslinkable vinyl monomer is less than 20 wt % based on the total amount of the monomers, the packing material may break at a high flow rate due to a decrease in strength, so that the column pressure may increase. If the amount of the crosslinkable vinyl monomer exceeds 50 wt % based on the total amount of the monomers, it may be difficult to control the pore size, and the binding capacity may decrease.

The affinity chromatography packing material according to one embodiment of the invention may include an additional vinyl monomer as the copolymer component preferably in an amount of 0 to 30 wt %.

The affinity chromatography packing material according to one embodiment of the invention preferably has a particle size (volume average particle size) of 20 to 80 micrometers, and more preferably 30 to 60 micrometers. If the particle size of the affinity chromatography packing material is less than 20 micrometers, the column pressure may increase to an impractical level at a high flow rate. If the particle size of the affinity chromatography packing material exceeds 80 micrometers, the binding capacity may deteriorate. Note that the "particle size" used herein refers to a volume average particle size determined using a laser diffraction/scattering particle size distribution analyzer.

The affinity chromatography packing material according to one embodiment of the invention preferably has a specific surface area of 50 to 150 $m^2/g$, and more preferably 80 to 120 $m^2/g$. If the specific surface area of the affinity chromatography packing material is less than 50 $m^2/g$, the binding capacity may deteriorate. If the specific surface area of the affinity chromatography packing material exceeds 150 $m^2/g$, the packing material may break at a high flow rate due to a decrease in strength, so that the column pressure may increase. Note that the "specific surface area" used herein refers to a value obtained by dividing the surface area of pores having a pore size of 10 to 5000 nm determined using a mercury porosimeter by the dry weight of the particles.

The affinity chromatography packing material according to one embodiment of the invention preferably has a volume average pore size of 100 to 400 nm, and more preferably 200 to 300 nm. If the volume average pore size of the affinity chromatography packing material is less than 100 nm, the binding capacity may significantly deteriorate at a high flow rate. If the volume average pore size of the affinity chromatography packing material exceeds 400 nm, the binding capacity may deteriorate irrespective of the flow rate. Note that the "volume average pore size" used herein refers to the volume average pore size of pores having a pore size of 10 to 5000 nm determined using a mercury porosimeter.

If the particle size, the specific surface area, and the pore size distribution of the affinity chromatography packing material are within the above ranges, the balance between the opening between the particles that serves as a passage for the purification target solution, a relatively large pore size in the particles, and the binding surface area of the purification target molecules is optimized, so that a high binding capacity is maintained at a high flow rate.

Specific examples of the porous mother particles used as the affinity chromatography packing material according to one embodiment of the invention include porous organic polymer particles including a copolymer of 20 to 50 wt % of a crosslinkable vinyl monomer and 50 to 80 wt % of an epoxy group-containing vinyl monomer, and having a particle size of 20 to 80 micrometers, a specific surface area of 50 to 150 $m^2/g$, and a volume average pore size of 100 to 400 nm.

The pore volume of pores having a pore size of 10 to 5000 nm when measuring the affinity chromatography packing material according to one embodiment of the invention using a mercury porosimeter is preferably 1.3 to 2.5 ml/g.

1.1.2. Production

The porous mother particles used as the affinity chromatography packing material according to one embodiment of the invention may be produced by seed polymerization, suspension polymerization, or the like. A two-stage swelling polymerization method disclosed in JP-B-57-24369 may suitably be used for seed polymerization. When producing the porous mother particles, the monomers, water, and a porogen are used as essential components, and a polymerization initiator, a polymer dispersant, a surfactant, a salt, seed particles, and the like are optionally used.

Examples of the porogen include organic solvents such as aliphatic or aromatic hydrocarbons, esters, ketones, ethers, and alcohols. Examples of the organic solvent include toluene, ethylbenzene, cumene, n-propylbenzene, n-butylbenzene, t-butylbenzene, sec-butylbenzene, isobutylbenzene, xylene, ethyltoluene, cymene, t-butyltoluene, diisopropylbenzene, mesitylene, cyclohexane, octane, isooctane, butyl acetate, dimethyl phthalate, methyl ethyl ketone, 2-octanone, 3-octanone, 4-octanone, diisobutyl ketone, 2-nonanone, 3-nonanone, 4-nonanone, 5-nonanone, 2-decanone, 3-decanone, 4-decanone, 5-decanone, 2-undecanone, 3-undecanone, 4-undecanone, 5-undecanone, 6-undecanone, phorone, isophorone, acetophenone, dibutyl ether, 1-hexanol, 2-octanol, decanol, lauryl alcohol, cyclohexanol, and the like. It is preferable to use a solvent that includes an aromatic hydrocarbon including an alkyl group having 2 or more carbon atoms as the main component, or a solvent that includes a ketone having 8 or more carbon atoms as the main component. It is most preferable to use a solvent that includes cumene and/or diisobutyl ketone as the main component. The pore size distribution and the specific surface area required for the packing material according to one embodiment of the invention can be obtained by appropriately selecting the amount and the type of the porogen depending on the monomer composition.

Examples of a preferable polymerization initiator include peroxide initiator such as benzoyl peroxide, lauroyl peroxide, tert-butyl peroxy-2-ethylhexanoate, and 3,5,5-trimethylhexanoyl peroxide, and azo initiator such as azobisisobutyronitrile and azobisisovaleronitrile. The polymerization initiator is dissolved in the monomer mixture or the porogen, and used for polymerization.

Examples of the polymer dispersant include water-soluble polymers such as polyvinyl alcohols having a degree of saponification of 80 to 95% and polyvinylpyrrolidone. Examples of the surfactant include anionic surfactants such as sodium dodecyl sulfate, sodium dodecylbenzene sulfonate, and polyoxyethylene dodecyl ether sulfate salts, nonionic surfactants such as polyoxyethylene alkyl ethers, and the like. Examples of a preferable salt include sodium chloride, sodium sulfate, and the like. Examples of the seed particles include polystyrene particles and poly(alkyl (meth)acrylate) particles having a molecular weight of about 1000 to 100,000. When using seed polymerization, the particle size required for the packing material according to one embodiment of the invention can be obtained by appropriately adjusting the size and the amount of the seed particles, the amount of the monomers, and the amount of the porogen. When using suspension polymerization, the particle size required for the packing material according to one embodiment of the invention can be obtained by appropriately adjusting the types and the amounts of the polymer dispersant and the surfactant, the stirring speed, and the shape and the size of a stirring blade and a polymerization vessel.

After completion of polymerization, the seed particles and/or the porogen are washed with a good solvent to obtain porous mother particles having the desired pore size distribution.

1.1.3. Binding of Ligand

A ligand is bound to the affinity chromatography packing material according to one embodiment of the invention.

For example, the ligand may be bound to the affinity chromatography packing material by (1) utilizing the epoxy group included in the porous mother particles as a ligand binding site (see JP-T-2006-511935, for example), (2) activating an alcoholic hydroxyl group produced by ring-opening of the epoxy group included in the porous mother particles using a tosyl group or the like, and binding the ligand to the porous mother particles, or causing the alcoholic hydroxyl group to undergo oxidative cleavage using an oxidizing agent, and binding the ligand to the porous mother particles (see JP-A-2007-211076 and JP-A-2008-032411, for example), or (3) forming a linker that extends from the epoxy group included in the porous mother particles or a group produced by ring-opening of the epoxy group, and binding the ligand to the porous mother particles via the linker (see JP-A-2008-032411, JP-A-10-195099, and JP-A-2004-331953, for example).

When using the above methods, the epoxy group present on the surface of the porous mother particles has been substantially ring-opened before the porous mother particles are used as the affinity chromatography packing material. Specifically, the affinity chromatography packing material according to one embodiment of the invention includes a ring-opening epoxy group. The ring-opening epoxy group is produced by ring-opening of the epoxy group included in the porous mother particles before or after binding the ligand to the porous mother particles. The term "ring-opening epoxy group" used herein refers to a group produced by ring-opening of an epoxy group. More specifically, the term "ring-opening epoxy group" used herein refers to a group produced by ring-opening of an epoxy group as a result of reacting the epoxy group with a nucleophilic compound that includes a hydroxide ion, a chloride ion, a mercapto group, an amino group, or the like, for example.

An alcoholic hydroxyl group produced by ring-opening of the epoxy group hydrophilizes the surface of the copolymer to prevent non-specific adsorption of proteins and the like, and improves the toughness of the particles in water to prevent breakage of the particles at a high flow rate. The epoxy group included in the porous mother particles may be ring-opened by stirring the porous mother particles in water with heating or at room temperature in the presence of an acid or alkali, for example. The epoxy group may also be ring-opened using a mercapto group-containing blocking agent (e.g., mercaptoethanol) or an amino group-containing blocking agent (e.g., monoethanolamine).

The ring-opening epoxy group may be a group produced by ring-opening of the epoxy group, a group obtained by binding the ligand to a group produced by ring-opening of the epoxy group, or a group obtained by binding the ligand to a group produced by ring-opening of the epoxy group via the linker (refer to the above methods (1) to (3)). The ring-opening epoxy group is preferably at least one of these groups. It is preferable that the porous mother particles include a substituted or unsubstituted 2,3-dihydroxypropyl group as the ring-opening epoxy group so that non-specific adsorption of proteins and the like can be more effectively prevented by hydrophilizing the surface of the copolymer. An unsubstituted 2,3-dihydroxypropyl group may be produced by ring-opening of a glycidyl group via hydrolysis, for example. A substituted 2,3-dihydroxypropyl group may be produced by ring-opening of a glycidyl group using a mercapto group-containing blocking agent (e.g., mercaptoethanol) or an amino group-containing blocking agent (e.g., monoethanolamine).

1.2. Ligand

The type of the ligand is not particularly limited insofar as the ligand has affinity to the target. Examples of the ligand include proteins such as protein A, protein G, and avidin; peptides such as insulin; antibodies such as monoclonal antibodies; enzymes; hormones; DNA; RNA; carbohydrates such as heparin, Lewis X, and ganglioside; and low-molecular-weight compounds such as iminodiacetic acid, synthetic dyes, 2-aminophenylboron acid, 4-aminobenzamidine, glutathione, biotin, and derivatives thereof. Note that fragments of these ligands obtained by recombination, an enzyme treatment, or the like may be used. It is also possible to use a synthetic peptide or a synthetic peptide derivative.

A ligand suitable for antibody purification is protein A and protein G, more preferably an immunoglobulin-binding domain of protein A, and most preferably a protein in which a peptide that includes four or more consecutive histidine units (SEQ ID NO: 20) is added to a terminal of an immunoglobulin-binding domain of protein A. Examples of such a protein include immunoglobulin-binding proteins shown by the following general formulas (1) and (3).

1.2.1. Immunoglobulin-Binding Protein

An immunoglobulin-binding protein shown by the following general formula (1) (hereinafter may be referred to as "protein 1") is preferable as the ligand.

$$R-R^2 \qquad (1)$$

wherein R represents an amino acid sequence that includes 4 to 300 amino acids and includes a site including 4 to 20 consecutive histidine residues (SEQ ID NO: 19), and $R^2$ represents an amino acid sequence that includes 50 to 500 amino acids and includes at least one immunoglobulin-binding domain of protein A, provided that a terminal of the immunoglobulin-binding domain binds to R.

The number of amino acids included in the amino acid sequence represented by R in the general formula (1) is preferably 8 to 100, and the number of histidine residues included in the site including consecutive histidine residues in the amino acid sequence represented by R is preferably 4 to 8 (SEQ ID NO: 21). The number of amino acids included in the amino acid sequence represented by $R^2$ in the general formula (1) is preferably 120 to 480.

R- in the general formula (1) is preferably a group shown by the following general formula (2).

$$R^1\text{-r-} \qquad (2)$$

wherein $R^1$ represents an amino acid sequence that includes 4 to 100 amino acids and includes a site including 4 to 20 consecutive histidine residues (SEQ ID NO: 19), provided that a terminal of the site including 4 to 20 consecutive histidine residues (SEQ ID NO: 19) binds to r, and r represents an arbitrary amino acid sequence that includes 7 to 200 amino acids and includes a TEV domain.

The number of amino acids included in the amino acid sequence represented by $R^1$ in the general formula (2) is preferably 4 to 25, the number of histidine residues included in the site including consecutive histidine residues in the amino acid sequence represented by $R^1$ is preferably 4 to 8 (SEQ ID NO: 21), and the number of amino acids included in the amino acid sequence represented by r is preferably 10 to 50.

An immunoglobulin-binding protein shown by the following general formula (3) (hereinafter may be referred to as "protein 2") is also preferable as the ligand.

$$R^2\text{-R} \qquad (3)$$

wherein R represents an amino acid sequence that includes 4 to 300 amino acids and includes a site including 4 to 20 consecutive histidine residues (SEQ ID NO: 19), and $R^2$ represents an amino acid sequence that includes 50 to 500 amino acids and includes at least one immunoglobulin-binding domain of protein A, provided that a terminal of the immunoglobulin-binding domain binds to R.

The number of amino acids included in the amino acid sequence represented by R in the general formula (3) is preferably 8 to 100, and the number of histidine residues included in the site including consecutive histidine residues in the amino acid sequence represented by R is preferably 4 to 8 (SEQ ID NO: 21). The number of amino acids included in the amino acid sequence represented by $R^2$ in the general formula (1) is preferably 120 to 480.

It is preferable that -R in the general formula (3) be a group shown by the following general formula (4).

$$\text{-r-}R^1 \qquad (4)$$

wherein $R^1$ represents an amino acid sequence that includes 4 to 100 amino acids and includes a site including 4 to 20 consecutive histidine residues (SEQ ID NO: 19), provided that a terminal of the site including 4 to 20 consecutive histidine residues (SEQ ID NO: 19) binds to r, and r represents an arbitrary amino acid sequence that includes 7 to 200 amino acids and includes a TEV domain.

The number of amino acids included in the amino acid sequence represented by $R^1$ in the general formula (4) is preferably 4 to 25, the number of histidine residues included in the site including consecutive histidine residues in the amino acid sequence represented by r is preferably 4 to 8 (SEQ ID NO: 21), and the number of amino acids included in the amino acid sequence represented by r is preferably 10 to 50.

It is preferable that at least one of the amino acid sequence represented by R and the amino acid sequence represented by $R^2$ in the general formulas (1) and (3) include a domain t that includes 1 to 50 amino acids and includes one amino acid selected from lysine, arginine, and cysteine. In this case, the amino acid sequence may include a plurality of identical or different domains t.

The amino acid sequence represented by r in the general formulas (2) and (4) may include a TEV domain. When the TEV domain is included in the amino acid sequence represented by r, the amino acid sequence represented by R and the amino acid sequence represented by $R^2$ can be separated by the TEV protease. Moreover, the TEV domain is a preferable sequence for achieving the effects (i.e., an increase in the amount of immobilization on a carrier, and an increase in immunoglobulin retention capability of the carrier) of the invention. The amino acid sequence represented by r may include a TEV mutant that has a homology of 70% or more, and preferably 90% or more with the amino acid sequence of the TEV domain (irrespective of whether or not breakage occurs due to the TEV protease).

The total number of amino acids of the protein 1 or 2 is normally 70 to 1000, and preferably 80 to 600 (when the protein 1 or 2 is bound to particles).

1.2.1.1. Immunoglobulin-Binding Domain

The immunoglobulin-binding domain of protein A is preferably at least one immunoglobulin-binding domain selected from an A-domain, a B-domain, a C-domain, a D-domain, an E-domain, and a Z-domain. The amino acid sequences of the A-domain, the B-domain, the C-domain, the D-domain, the E-domain, and the Z-domain are disclosed in FIG. 1 of Moks T, Abrahms L, et al., Staphylococcal protein A consists of five IgG-binding domains, Eur J. Biochem. 1986, 156, 637-643. The disclosure of the above document is incorporated herein by reference. A protein that includes an amino acid sequence having a homology of 70% or more (preferably 90% or more) with the amino acid sequence of each domain disclosed in the above document may also be the immunoglobulin-binding domain of protein A.

The immunoglobulin-binding protein may include a plurality of identical or different immunoglobulin-binding domains. For example, the immunoglobulin-binding domain of protein A may include (D-domain-A-domain)n (wherein n is an integer equal to or larger than 1 (preferably an integer from 1 to 6), and an arbitrary amino acid sequence may be present between the D-domain and the A-domain) (i.e., a repeating unit that includes the A-domain and the D-domain).

The immunoglobulin-binding domain of protein A may be a natural immunoglobulin-binding domain, or may be a recombinant immunoglobulin-binding domain. The recombinant immunoglobulin-binding domain is considered to have an immunoglobulin avidity equal to that of the unaltered immunoglobulin-binding domain. For example, the amino acid sequence of the recombinant immunoglobulin-binding domain preferably has a homology of 70% or more (preferably 90% or more) with the amino acid sequence of a natural immunoglobulin-binding domain of protein A. Specific examples of the recombinant immunoglobulin-binding domain include the Z-domain disclosed in Nilsson B. et al., Protein engineering, 1987, vol. 1, No. 2, pp. 107 to 113, and the alkali-resistant Z-domain mutant disclosed in U.S. Patent Publication No. 2006/0194955 (Hober et al.). The disclosure of the above documents is incorporated herein by reference. A protein that includes an amino acid sequence having a homology of 70% or more (preferably 90% or more) with the amino acid sequence of each domain disclosed in the above documents may also be the immunoglobulin-binding domain of protein A.

1.2.1.2. Production of Protein 1 or 2

The protein 1 or 2 may be produced by known gene recombination techniques such as those disclosed in Frederick M. Ausbel et al., Current Protocols In Molecular Biology, Sambrook et al. (editor), Molecular Cloning (Cold Spring Harbor Laboratory Press, 3rd edition, 2001), and the like. For example, the protein 1 or 2 may be produced by the gene recombination technology disclosed in U.S. Pat. No. 5,151, 350. Specifically, an expression vector that includes a nucleic acid sequence that encodes the target protein (protein 1 or 2) is transformed into host cells (e.g., *Escherichia coli*), and the cells are cultured in an appropriate liquid medium. A large amount of protein 1 or 2 can be economically obtained from the cultured cells. Examples of a preferable expression vector include known vectors that replicate in bacteria. For example, the plasmid disclosed in U.S. Pat. No. 5,151,350, the plasmid disclosed in Sambrook et al. (editor), Molecular Cloning (Cold Spring Harbor Laboratory Press, 3rd edition, 2001), or the like may be used. A nucleic acid may be introduced into bacteria by an arbitrary method to effect transformation. For example, the method disclosed in Sambrook et al. (editor), Molecular Cloning (Cold Spring Harbor Laboratory Press, 3rd edition, 2001), or the like may be used. The transformed bacteria may be cultured, and the expressed proteins may be collected by a well-known method.

Specifically, a nucleic acid according to one embodiment of the invention encodes the immunoglobulin-binding protein (protein 1 or 2) or a functional variant thereof. The term "functional variant" of an immunoglobulin-binding protein used herein refers to an immunoglobulin-binding protein that has been altered (modified) by addition, deletion, or substitution of an amino acid, chemical modification of an amino acid residue, or the like, includes an amino acid sequence having a homology of 70% or more, and preferably 90% or more with the amino acid sequence of the unaltered immunoglobulin-binding protein, and is considered to have an immunoglobulin avidity equal to that of the unaltered immunoglobulin-binding protein.

Specifically, since a single immunoglobulin-binding domain of protein A is a small protein that includes about 60 amino acids, the target expression vector can be obtained by synthesizing a DNA that encodes the desired amino acid sequence as synthetic oligonucleotides that include several tens of bases, binding the oligonucleotides by a ligation reaction using a DNA ligase, and inserting it into a plasmid. In this case, a nucleic acid sequence using optimum codons of *Escherichia coli* is normally employed so that the protein is efficiently expressed in *Escherichia coli*. It is also possible to obtain a DNA sequence that encodes the desired amino acid sequence from the *Straphylococcus aureus* genomic DNA by the polymerase chain reaction (PCR).

The protein 1 or 2 may be a protein that includes one or more (preferably 2 to 12, and more preferably 2 to 5) immunoglobulin-binding domains. A cDNA that encodes such a protein may be easily obtained by linking a given number of pieces of complementary DNA (cDNA) that encodes a single immunoglobulin-binding domain in series. A protein that includes one or more immunoglobulin-binding domains can be easily produced by inserting the resulting cDNA into an appropriate expression plasmid.

For example, a protein having an amino acid sequence of any of SEQ ID NO: 1 to SEQ ID NO: 8 (see the examples), or a protein having an immunoglobulin avidity and having an amino acid sequence of any of SEQ ID NO: 1 to SEQ ID NO: 8 in which one or more amino acids are deleted, substituted, or added may suitably be used as the immunoglobulin-binding protein according to one embodiment of the invention.

1.2.1.3. Effects

An affinity chromatography packing material that utilizes the protein 1 or 2 as a ligand advantageously retains a large amount of immunoglobulin-binding proteins as compared with a related-art packing material. This increases the amount of the target proteins to be captured, so that the binding capacity for the target proteins (antibodies) can be increased. This makes it possible to efficiently and inexpensively purify a large amount of the target proteins having high purity.

2. Examples

The affinity chromatography packing material according to one embodiment of the invention is further described below by way of examples. Note that the following examples generally illustrate an aspect of the invention, and the invention is not limited to the following examples.

2.1. Evaluation Method

2.1.1. Particle Size

The volume average particle size of the particles was determined using a laser diffraction/scattering particle size distribution analyzer ("LS13320" manufactured by Beckman Coulter, Inc.).

2.1.2. Specific Surface Area, Volume Average Pore Size, and Modal Pore Size The affinity chromatography packing materials produced in Synthesis Examples 4 to 8 and Comparative Synthesis Example 1 were dried at 40° C. for 24 hours under vacuum to obtain dry particles, and the specific surface area, the volume average pore size, and the modal pore size of the dry particles were determined using a mercury porosimeter ("AutoPore IV9520" manufactured by Shimadzu Corporation). The measurement range was 10 to 5000 nm (pore size).

2.1.3. Binding Capacity

2.1.3.1. Measurement Method 1

The human IgG antibody binding capacity was measured at a linear flow rate of 150 cm/hr, 500 cm/hr, and 1000 cm/hr using an instrument "AKTAprime plus" (manufactured by GE Healthcare Biosciences). The column volume was 1 ml. The human IgG antibody (manufactured by Lampire Biological Laboratories) was diluted to 1 mg/ml with a 25 mM citrate buffer (pH: 6.0). The binding capacity was calculated from the adsorption amount of the human IgG antibody and the volume of the packing material at an elution concentration of 5 w/v % (breakthrough) measured using an absorbance monitor.

2.1.3.2. Measurement Method 2

The human IgG antibody binding capacity was measured at a linear flow rate of 300 cm/hrr using a column having an inner diameter of 0.5 cm and a height of 5 cm and an instrument "AKTAprime plus" (manufactured by GE Healthcare Biosciences). The human IgG antibody (manufactured by Lampire Biological Laboratories) was diluted to 1 mg/ml with a 25 mM citrate buffer (pH: 6.0). The binding capacity was calculated from the adsorption amount of the human IgG antibody and the volume of the packing material at an elution concentration of 10 w/v % (breakthrough) measured using an absorbance monitor.

2.2. Experimental Examples

2.2.1. Synthesis Example 1 (Production of Immunoglobulin-Binding Protein)

Immunoglobulin-binding proteins respectively having amino acid sequences illustrated in FIGS. 1 and 2 (SPAK (SEQ ID NO: 1), SPAC (SEQ ID NO: 2), SPAKK (SEQ ID NO: 3), SPATK (SEQ ID NO: 4), SPA2K (SEQ ID NO: 5), SPA3K (SEQ ID NO: 6), SPA-His-C (SEQ ID NO: 7), and SPA-His-N (SEQ ID NO: 8)) were produced in Production Examples 1 to 4.

In FIGS. 1 and 2, R and $R^2$ respectively correspond to R and $R^2$ in the general formulas (1) or (2) ($R^1$, $R^2$, and r respectively correspond to $R^1$, $R^2$, and r in the general formula (2) or (4)), an underline in r indicates a TEV domain (TEV protease (peptide bond hydrolase) cleavage site), and an underline in $R^2$ indicates an interdomain linker or a C-terminal linker (domain t) (see Table 2).

It was confirmed by MALDI-TOF mass spectrum analysis that these proteins respectively had the amino acid sequences illustrated in FIGS. 1 and 2.

2.2.1.1. Production Example 1 (PCR Amplification and Restriction Endonuclease Digestion)

The cDNA of protein A (D-domain+A-domain) derived from *Straphylococcus aureus* (ATCC,10832) was amplified by PCR. Primers (see Table 2) were designed to have a corresponding restriction endonuclease site in order to assist subcloning (described later).

The DNA fragments respectively encoding the immunoglobulin-binding proteins SPAK, SPAC, SPA2K, SPA3K, SPAKK, and SPATK were digested by restriction endonucleases NcoI and HindIII (manufactured by New-England Bio Lab), and inserted into a vector pETM-11 (see FIG. 3, obtained from kind gift of D. Shibly, EMBL Heidelberg, Heidelberg, Germany) (see Table 1).

The DNA fragment encoding the immunoglobulin-binding protein SPA-His-N was digested by restriction endonucleases NcoI and HindIII, and inserted into a vector pETM-10 (see FIG. 3, obtained from kind gift of D. Shibly, EMBL Heidelberg, Heidelberg, Germany) (see Table 1).

A vector pET29 (see FIG. 3, manufactured by Novagen) was used to produce the immunoglobulin-binding protein SPA-His-C having a histidine tag (peptide consisting of six histidine residues (SEQ ID NO: 22)) at the C-terminal (see Table 1). Restriction endonucleases NdeI (manufactured by New-England Bio Lab) and XhoI (manufactured by New-England Bio Lab) were used for the vector pET29.

Each of the expression vectors illustrated in FIG. 3 includes a kanamycin resistance gene as a selection marker.

"Tev" in the amino acid sequence of the immunoglobulin-binding protein illustrated in FIG. 3 indicates a TEV protease recognition site (amino acid sequence: ENLYFQG (SEQ ID NO: 23)). The TEV protease recognizes the amino acid sequence ENLYFQG (SEQ ID NO: 23), and cleaves the amino acid sequence ENLYFQG (SEQ ID NO: 23) between Q and G.

The restriction endonucleases were introduced by designing a pair of primers based on the insertion sequence of the immunoglobulin-binding protein SPAK. PCR amplification was performed using the primers (SEQ ID NO: 9 to SEQ ID NO: 17) shown in Table 2.

Note that the DNA fragment of the immunoglobulin-binding protein SPA-His-N may be directly obtained by digesting a plasmid including the immunoglobulin-binding protein SPAK using restriction endonucleases (see Table 1). In Synthesis Example 1, the DNA fragment of the immunoglobulin-binding protein SPA-His-N was directly obtained by digesting a plasmid including the immunoglobulin-binding protein SPAK using restriction endonucleases (see Table 1).

TABLE 1

| Immunoglobulin-binding protein | Expression vector | Restriction endonuclease I |
| --- | --- | --- |
| SPAK | pETM-11 | Nco I and Hind III |
| SPAC | pETM-11 | Nco I and Hind III |
| SPAKK | pETM-11 | Nco I and Hind III |
| SPATK | pETM-11 | Nco I and Hind III |
| SPA2K | pETM-11 | Nco I and Hind III |
| SPA3K | pETM-11 | Nco I and Hind III |
| SPA-His-C | pET29 | Nde I and Xho I |
| SPA-His-N | pETM-10 | Nco I and Hind III |

Fermentas), and 1 microliter of a Pfu polymerase (manufactured by Fermentas) (5 units/microliter) so that the final volume of the mixture was 50 microliters. PCR amplification was performed in 30 cycles (one cycle: 94° C. for 1 minute, 94° C. for 30 seconds, 56° C. for 1 minute, and 72° C. for 1 minute), and then performed at 72° C. for 10 minutes. The PCR reaction was implemented using a PX2 Thermal Cycler PCR system (manufactured by Thermo Electron Corporation).

2.2.1.2. Production Example 2 (Ligation and Transformation)

The DNA fragment digested by the restriction endonucleases was ligated at 12° C. for 12 to 16 hours using 100 to 200 units/ml of a T4DNA ligase (manufactured by New England Biolab) and a 5× ligase buffer (manufactured by New England Bio lab). *E. coli* DH 5-alpha cells (manufactured by New England Biolab) were used for plasmid transformation.

2.2.1.3. Production Example 3 (Production of Plasmid DNA and Sequence Analysis)

A positive colony was selected, and plasmid DNA was extracted using a Mini Prep Kit (manufactured by Qiagen). The sequence of the plasmid DNA was analyzed using a 3730 NDA Sequencer (manufactured by Applied Biosystems) in order to determine whether or not the inserted DNA fragment had a correct sequence.

2.2.1.4. Production Example 4 (Expression and Purification of Immunoglobulin-Binding Protein)

1 mM IPTG (manufactured by Sigma-Aldrich) was added to *E. coli* (BL21) cells (manufactured by STRATAGENE) at 18° C., and a recombinant immunoglobulin-binding protein

TABLE 2

| Primer | SEQ ID NO: | Sequence | Product |
| --- | --- | --- | --- |
| Fwd NcoI | 9 | 5'-CAT GCC ATG GCG AAA GCT GAT GCG CAA CAA AAT-3' | SPAK, SPAC, SPA2K, SPA3K, SPAKK, SPATK |
| Rev Lys-HindIII | 10 | 5'-CCC AAG CTT TTA CTT GGA TCC TTC TTT GTT GAA TTT GTT ATC CG-3' | SPAK |
| Rev Cyc-HindIII | 11 | 5'-CCC AAG CTT TTA GCA GGA TCC TTC TTT GTT GAA TTT GTT ATC CG-3' | SPAC |
| Rev 2k HindIII | 12 | 5'-CCC AAG CTT TTA CTT CTT GGA TCC TTC TTT GTT GAA TTT GTT AT-3' | SPA2K |
| Rev 3k Hind III | 13 | 5'-CCC AAG CTT TTA CTT CTT CTT GGA TCC TTC TTT GTT GAA TTT GTT AT-3' | SPA3K |
| Rev pol K Hind III | 14 | 5'-CCC AAG CTT TTA TTT CTT TTT CTT CTT GGA TCC TTC TTT GTT GAA TTT GTT AT-3' | SPAKK |
| Rev Wd-T-GC-Linker-BamHI | 15 | 5'-CGG GGA TCC TCA GGC AAA GCT GAT GCG CAA CAA AAT-3' | SPATK |
| Fwd Nde I | 16 | 5'-CCC CAT ATG GCG AAA GCT GAT GCG CAA A-3' | SPA-His-C |
| Rev Xho I | 17 | 5'-GGG CTC GAG CTT GGA TCC TTC TTT GTT-3' | SPA-His-C |

Sterilized water was added to a PCR amplification solution containing 0.5 microliters of a *Straphylococcus aureus* genomic DNA template (500 ng/microliters), 5 pl of each primer, 5 microliters of a 10×Pfu buffer (manufactured by was expressed for 15 hours. The cells were incubated at 37° C. before induction until the absorbance (OD600) reached about 0.6. The cells were collected after the protein had been expressed, and fractured in a Tris buffer (pH: 8.0).

The resulting recombinant immunoglobulin-binding protein was purified by Ni affinity chromatography (Ni-NTA (nitrilotriacetic acid) particles manufactured by Qiagen). The purified immunoglobulin-binding protein was further purified in an HEPES buffer (pH: 7.5) by anion exchange chromatography (Q-sepharose FF manufactured by GE Healthcare Biosciences).

2.2.2. Synthesis Example 2 (Immobilization of Immunoglobulin-Binding Protein on Particles)

2.2.2.1. Immobilization Example 1

Porous particles (hereinafter referred to as "PB") formed of a glycidyl methacrylate-trimethylolpropane trimethacrylate copolymer were produced by suspension polymerization. The porous particles PB had an average particle size of 33 micrometers, and a specific surface area of 83 $m^2/g$. A mixture prepared by dispersing 400 mg of the porous particles PB and 36 mg of the immunoglobulin-binding protein SPAK in 16 ml of a borate buffer (pH: 8.5) was inversion-mixed at 4° C. for 24 hours so that the immunoglobulin-binding protein SPAK was bound to the porous particles PB. After the addition of 0.8 ml of a 10% mercaptoethanol aqueous solution, the mixture was inversion-mixed at 4° C. for 6 hours to ring-open and block the remaining epoxy groups. The particles were washed with a 20% ethanol aqueous solution to obtain 380 mg of SPAK-bound porous particles (SPAK-PB). The amount of the immunoglobulin-binding protein SPAK bound to the particles determined using a Thermo Scientific Pierce BCA Protein Assay kit was 29 mg/g particle.

2.2.2.2. Immobilization Example 2

The immunoglobulin-binding protein SPAK digested by a TEV protease was passed through an Ni-NAT column (volume: 4 ml) in a buffer (pH: 8.0) containing 50 mM trishydrochloric acid, 0.5 mM EDTA, and 1 mM DTT to collect a crude immunoglobulin-binding protein SPAKwoHis in which the histidine tag of the immunoglobulin-binding protein SPAK was cleaved. The crude immunoglobulin-binding protein SPAKwoHis was dialyzed in a 10 mM HEPES buffer (pH: 7.5) for 12 hours to obtain a binding assay immunoglobulin-binding protein SPAKwoHis. The amino acid sequence of the immunoglobulin-binding protein SPAKwoHis was as follows.

```
SPAKwohis (complete amino acid sequence)
                                (SEQ ID NO: 18)
GAMAKADAQQNNFNKDQQSAFYEILNMPNLNEAQRNGFIQSLKDDPSQST

NVLGEAKKLNESQAPKADNNFNKEQQNAFYEILNMPNLNEEQRNGFIQSL

KDDPSQSANLLSEAKKLNESQAPKADNKFNKEGSK
```

380 mg of SPAKwoHis-bound porous particles (SPAKwoHis-PB) were obtained in the same manner as in Immobilization Example 1, except for using the immunoglobulin-binding protein SPAKwoHis instead of the immunoglobulin-binding protein SPAK. The amount of the immunoglobulin-binding protein SPAKwoHis bound to the particles was 6 mg/g particle.

2.2.2.3. Immobilization Example 3

380 mg of SPATK-bound porous particles (SPATK-PB) were obtained in the same manner as in Immobilization Example 1, except for using the immunoglobulin-binding protein SPATK instead of the immunoglobulin-binding protein SPAK. The amount of the immunoglobulin-binding protein SPATK bound to the particles was 36 mg/g particle.

2.2.3. Test Examples (Measurement of Immunoglobulin G (IgG) Binding Amount)

2.2.3.1. Measurement Example 1

The human IgG antibody binding capacity of the SPAK-bound porous particles SPAK-PB determined by the method described in the section entitled "2.1.3.1. Measurement method 1" was 30 mg/ml.

2.2.3.2. Measurement Example 2

The human IgG antibody binding capacity of the SPATK-bound porous particles SPAK-PB determined by the method described in the section entitled "2.1.3.1. Measurement method 1" was 35 mg/ml.

2.2.3.3. Measurement Example 3

The human IgG antibody binding capacity of the SPAK-woHis-bound porous particles SPAKwoHis-PB determined by the method described in the section entitled "2.1.3.1. Measurement method 1" was 6 mg/ml.

2.2.4. Synthesis Example 3 (Production of Affinity Chromatography Packing Material)

(i) Synthesis of porous mother particles: 60 g of glycidyl methacrylate (manufactured by Mitsubishi Rayon Co., Ltd.) and 40 g of trimethylolpropane trimethacrylate (manufactured by Sartomer) were dissolved in 173 g of diisobutyl ketone (manufactured by Mitsui Chemicals Inc.) and 67 g of acetophenone (manufactured by Wako Pure Chemical Industries, Ltd.). 1 g of 2,2'-azoisobutyronitrile (manufactured by Wako Pure Chemical Industries, Ltd.) was added to the solution to prepare an organic monomer solution.

12 g of polyvinyl alcohol ("PVA-217" manufactured by Kuraray Co., Ltd.), 1 g of sodium dodecyl sulfate ("Emal 10G" manufactured by Kao Corporation), and 31 g of sodium chloride were added to 3000 g of purified water The mixture was stirred overnight to prepare an aqueous solution.

A separable flask (7 l) was charged with the resulting aqueous solution. The separable flask was equipped with a thermometer, a stirring blade, and a cooling tube, and placed in a hot water bath. The aqueous solution was then stirred at 825 rpm in a nitrogen atmosphere. When the temperature of the aqueous solution had reached 85° C., the organic monomer solution was added to the aqueous solution using a dropping funnel. The mixture was then stirred for 5 hours.

The reaction solution was then cooled, and transferred to a polypropylene bottle (5l). The reaction solution was then allowed to stand until the particles floated, and unnecessary water was sucked out from the bottom of the bottle. Acetone was then added to the reaction solution to precipitate the particles. After allowing the reaction solution to stand for 3 minutes, acetone was removed by decantation. After repeating this operation twice, water was added to precipitate the particles. After allowing the mixture to stand for 3 minutes, the mixture was subjected to decantation. After repeating this operation twice, the particles were washed. After replacing the dispersion medium of the particle dispersion with acetone, the mixture was air-dried overnight. The mixture was then dried using a vacuum dryer to obtain porous mother particles 1 (86 g).

(ii) Production of Ligand

The immunoglobulin-binding protein SPAK produced in Synthesis Example 1 was used as a ligand 1.

(iii) Binding of Ligand to Porous Mother Particles

A mixture prepared by dispersing 350 mg of the porous mother particles 1 and 18 ml of the ligand 1 in 18 ml of a borate buffer (pH: 8.5) was inversion-mixed at 4° C. for 20 hours so that the ligand 1 was bound to the porous mother particles 1. The mixture was washed twice with 20 ml of an aqueous solution containing 0.5 mol/l of mercaptoethanol and 0.5 mol/l of sodium chloride, and inversion-mixed at room temperature for 4 hours in 20 ml of a buffer (pH: 8.5) containing 0.5 mol/l of mercaptoethanol and 0.5 mol/l of sodium chloride to ring-open and block the remaining epoxy groups. The mixture was then washed with a 20% ethanol aqueous solution to obtain 320 of an affinity chromatography packing material 1.

(iv) Evaluation

The affinity chromatography packing material 1 had a particle size of 43 micrometers, a specific surface area of 64 m²/g, a volume average pore size of 235 nm, a modal pore size of 130 nm, and a ratio "volume average pore size/modal pore size" of 1.8. The binding capacity calculated by the method described in the section entitled "2.1.3.2. Measurement method 2" was 26 mg/ml at 150 cm/hr, 23 mg/ml at 500 cm/hr, and 22 mg/ml at 1000 cm/hr.

2.2.5. Synthesis Example 4

An affinity chromatography packing material 2 was obtained in the same manner as in Synthesis Example 3, except for using 115 g of diisobutyl ketone and 45 g of acetophenone instead of 173 g of diisobutyl ketone and 67 g of acetophenone, and using a separable flask equipped with a baffle instead of the separable flask.

The affinity chromatography packing material 2 had a particle size of 33 micrometers, a specific surface area of 83 m²/g, a volume average pore size of 146 nm, a modal pore size of 40 nm, and a ratio "volume average pore size/modal pore size" of 3.7. The binding capacity calculated by the method described in the section entitled "2.1.3.2. Measurement method 2" was 32 mg/ml at 150 cm/hr, 20 mg/ml at 500 cm/hr, and 14 mg/ml at 1000 cm/hr.

2.2.6. Synthesis Example 5

An affinity chromatography packing material 3 was obtained in the same manner as in Synthesis Example 3, except that the ligand was bound to the porous mother particles as follows.

(i) Binding of Ligand to Porous Mother Particles 10 g of the porous mother particles 1 were put in a polyethylene bottle (250 ml), and dispersed in 80 g of purified water. 10 g of 0.1 M sulfuric acid was then added to the mixture. The resulting mixture was inversion-mixed at 60° C. for 5 hours to ring-open the epoxy groups of the porous mother particles 1. The mixture was then filtered using a Kiriyama funnel. The porous mother particles 1 were washed with purified water and acetonitrile, and dispersed in 200 g of acetonitrile. After the addition of 1.3 g of tosyl chloride, 1.3 g of tripropylamine, and 0.8 g of trimethylamine hydrochloride, the mixture was stirred at room temperature for 5 hours to tosylate the hydroxyl groups. The mixture was then filtered. The particles were washed with acetonitrile and water, and dispersed in 90 g of a borate buffer (pH: 9.5) to obtain a dispersion of 10 g of tosylated porous mother particles 1. A mixture prepared by dispersing 400 mg of tosylated porous mother particles 1 and 36 mg of the ligand 1 in 16 ml of a borate buffer was inversion-mixed at 37° C. for 20 hours so that the ligand 1 was bound to the tosylated porous mother particles 1. After the addition of 0.8 ml of a 10% monoethanolamine aqueous solution, the mixture was inversion-mixed at 37° C. for 6 hours to block the remaining tosyl groups. The particles were washed with a 20% ethanol aqueous solution to obtain 380 mg of the affinity chromatography packing material 3.

(ii) Evaluation

The affinity chromatography packing material 3 had a particle size of 43 micrometers, a specific surface area of 64 m²/g, a volume average pore size of 235 nm, a modal pore size of 130 nm, and a ratio "volume average pore size/modal pore size" of 1.8. The binding capacity calculated by the method described in the section entitled "2.1.3.2. Measurement method 2" was 25 mg/ml at 150 cm/hr, 21 mg/ml at 500 cm/hr, and 20 mg/ml at 1000 cm/hr.

2.2.7. Synthesis Example 6

An affinity chromatography packing material 4 was obtained in the same manner as in Synthesis Example 3, except for using 140 g of cumene and 20 g of acetophenone instead of 173 g of diisobutyl ketone and 67 g of acetophenone.

The affinity chromatography packing material 4 had a particle size of 39 micrometers, a specific surface area of 91 m²/g, a volume average pore size of 128 nm, a modal pore size of 33 nm, and a ratio "volume average pore size/modal pore size" of 3.9. The binding capacity calculated by the method described in the section entitled "2.1.3.2. Measurement method 2" was 19 mg/ml at 150 cm/hr, 8 mg/ml at 500 cm/hr, and 6 mg/ml at 1000 cm/hr.

2.2.8. Synthesis Example 7

An affinity chromatography packing material 5 was obtained in the same manner as in Synthesis Example 3, except for using 15 g of trimethylolpropane trimethacrylate and 25 g of ethylene glycol dimethacrylate instead of 40 g of trimethylolpropane trimethacrylate, and using 115 g of diisobutyl ketone and 45 g of acetophenone instead of 173 g of diisobutyl ketone and 67 g of acetophenone.

The affinity chromatography packing material 2 had a particle size of 32 micrometers, a specific surface area of 38 m²/g, a volume average pore size of 329 nm, a modal pore size of 302 nm, and a ratio "volume average pore size/modal pore size" of 1.1. The binding capacity calculated by the method described in the section entitled "2.1.3.2. Measurement method 2" was 10 mg/ml at 150 cm/hr, 9 mg/ml at 500 cm/hr, and 8 mg/ml at 1000 cm/hr.

2.2.9. Synthesis Example 8

An affinity chromatography packing material 6 was obtained in the same manner as in Synthesis Example 3, except for using the immunoglobulin-binding protein SPAK-woHis instead of the ligand 1.

The affinity chromatography packing material 6 had a particle size of 33 micrometers, a specific surface area of 83 m²/g, a volume average pore size of 146 nm, a modal pore size of 40 nm, and a ratio "volume average pore size/modal pore size" of 3.7. The binding capacity calculated by the method described in the section entitled "2.1.3.2. Measurement method 2" was 8 mg/ml at 150 cm/hr, 5 mg/ml at 500 cm/hr, and 4 mg/ml at 1000 cm/hr.

2.2.10. Comparative Synthesis Example 1

An affinity chromatography packing material ("MabSelect Xtra" manufactured by GE Healthcare Biosciences) in which protein A was immobilized on crosslinked agarose (i.e., a vinyl monomer was not used as the raw material) was evaluated in the same manner as described above. The binding capacity calculated by the method described in the section entitled "2.1.3.2. Measurement method 2" was 25 mg/ml at 150 cm/hr, and 12 mg/ml at 500 cm/hr. Note that a linear flow rate of 1000 cm/hr could not be reached due to high column pressure.

The embodiments according to the invention have been described above. Note that the invention is not limited to the above embodiments. Various modifications and variations may be made. The invention includes various other configurations substantially the same as the configurations described in connection with the embodiments (such as a configuration having the same function, method, and results, or a configuration having the same objective and results). The invention also includes a configuration in which an unsubstantial element described in connection with the above embodiments is replaced with another element. The invention also includes a configuration having the same effects as those of the configurations described in connection with the above embodiments, or a configuration capable of achieving the same objective as that of the configurations described in connection with the above embodiments. The invention also includes a configuration in which a known technique is added to the configurations described in connection with the above embodiments.

The invention claimed is:

1. An affinity chromatography packing material, comprising:
at least one porous mother particle that comprises a copolymer of a monomer mixture comprising a crosslinkable vinyl monomer and an epoxy group-comprising vinyl monomer,
wherein:
a ligand is bound to the porous mother particle;
the porous mother particle comprises a ring-opening epoxy group produced by ring-opening of the epoxy group comprised in the porous mother particles;
the ligand is bound to the porous mother particle by (i) utilizing the epoxy group comprised in the porous mother particles as a ligand binding site, (ii) activating an alcoholic hydroxyl group produced by ring-opening of the epoxy group comprised in the porous mother particles, and binding the ligand to the porous mother particles, or (iii) forming a linker that extends from the epoxy group comprised in the porous mother particles or a group produced by ring-opening of the epoxy group, and binding the ligand to the porous mother particles via the linker; and
the ligand is an immunoglobulin-binding protein of formula (1), $$R\text{-}R^2 \quad (1)$$

wherein
R represents an amino acid sequence that comprises 4 to 300 amino acids and a site including 4 to 20 consecutive histidine residues, and
$R^2$ represents an amino acid sequence that comprises 50 to 500 amino acids and at least one immunoglobulin-binding domain of protein A, provided that a terminal of the immunoglobulin-binding domain binds to R.

2. The affinity chromatography packing material of claim 1, wherein the ring-opening epoxy group is a substituted or unsubstituted 2,3-dihydroxypropyl group.

3. The affinity chromatography packing material of claim 1, wherein the immunoglobulin-binding domain of protein A is at least one immunoglobulin-binding domain selected from the group consisting of an A-domain, a B-domain, a C-domain, a D-domain, an E-domain, and a Z-domain.

4. The affinity chromatography packing material of claim 1, wherein R- in formula (1) is a group of formula (2), $$R^1\text{-r-} \quad (2)$$

wherein
$R^1$ represents an amino acid sequence that comprises 4 to 100 amino acids and a site comprising 4 to 20 consecutive histidine residues, provided that a terminal of the site comprising 4 to 20 consecutive histidine residues binds to r, and
r represents an arbitrary amino acid sequence that comprises 7 to 200 amino acids and a TEV domain.

5. The affinity chromatography packing material of claim 1, wherein at least one selected from the group consisting of the amino acid sequence represented by R and the amino acid sequence represented by $R^2$ in formula (1), comprises a domain t that comprises 1 to 50 amino acids and one amino acid selected from the group consisting of lysine, arginine, and cysteine.

6. The affinity chromatography packing material of claim 1, wherein the monomer mixture comprises:
20 to 50 wt% of the crosslinkable vinyl monomer; and
50 to 80 wt% of the epoxy group-comprising vinyl monomer.

7. The affinity chromatography packing material of claim 1, wherein the at least one porous mother particle has a volume average particle size of 20 to 80 micrometers.

8. The affinity chromatography packing material of claim 1, wherein the at least one porous mother particle has a volume average particle size of 30 to 60 micrometers.

9. The affinity chromatography packing material of claim 1, wherein the at least one porous mother particle has a specific surface area of 50 to 150 m²/g.

10. The affinity chromatography packing material of claim 1, wherein the at least one porous mother particle has a specific surface area of 80 to 120 m²/g.

11. The affinity chromatography packing material of claim 1, wherein the at least one porous mother particle has a volume average pore size of 100 to 400 nm.

12. The affinity chromatography packing material of claim 1, wherein the ring-opening epoxy group comprises a substituted 2,3-dihydroxypropyl group, wherein the substituted 2,3-dihydroxypropyl group is produced by ring-opening of the epoxy group comprised in the at least one porous mother particle with a mercapto group-comprising blocking agent.

13. The affinity chromatography packing material of claim 10, wherein the substituted 2,3-dihydroxypropyl group is produced by ring-opening of the epoxy group comprised in the at least one porous mother particle with mercaptoethanol.

14. The affinity chromatography packing material of claim 1, wherein the ring-opening epoxy group comprises a substituted 2,3-dihydroxypropyl group, wherein the substituted 2,3-dihydroxypropyl group is produced by ring-opening of the epoxy group comprised in the at least one porous mother particle with an amino group-comprising blocking agent.

15. The affinity chromatography packing material of claim 10, wherein the substituted 2,3-dihydroxypropyl group is produced by ring-opening of the epoxy group comprised in the at least one porous mother particle with monoethanolamine.

* * * * *